(12) United States Patent
Chen

(10) Patent No.: US 12,357,434 B2
(45) Date of Patent: Jul. 15, 2025

(54) MAXILLA HOLDER AND INSTALLATION THEREOF

(71) Applicant: Liang-Cheng Chen, Taichung (TW)

(72) Inventor: Liang-Cheng Chen, Taichung (TW)

( * ) Notice: Subject to any disclaimer, the term of this patent is extended or adjusted under 35 U.S.C. 154(b) by 0 days.

(21) Appl. No.: 18/813,861

(22) Filed: Aug. 23, 2024

(65) Prior Publication Data

US 2025/0064561 A1 Feb. 27, 2025

(30) Foreign Application Priority Data

Aug. 25, 2023 (TW) ................. 112132179

(51) Int. Cl.
| | | |
|---|---|---|
| A61B 17/66 | (2006.01) | |
| A61B 17/80 | (2006.01) | |
| A61B 17/88 | (2006.01) | |
| A61C 7/06 | (2006.01) | |
| A61C 11/00 | (2006.01) | |

(52) U.S. Cl.
CPC .......... *A61C 11/001* (2013.01); *A61B 17/663* (2013.01); *A61B 17/8071* (2013.01); *A61B 17/8866* (2013.01); *A61C 7/06* (2013.01)

(58) Field of Classification Search
CPC ... A61B 17/8071; A61B 17/66; A61B 17/663; A61B 17/666; A61B 17/1673; A61B 17/176
See application file for complete search history.

(56) References Cited

U.S. PATENT DOCUMENTS

| | | | | |
|---|---|---|---|---|
| 8,282,635 | B1* | 10/2012 | Amato | G09B 23/32 |
| | | | | 606/57 |
| 8,764,441 | B2* | 7/2014 | Polley | A61B 17/666 |
| | | | | 606/86 R |
| 9,333,053 | B2* | 5/2016 | Alyami | A61C 8/0096 |
| 9,339,279 | B2* | 5/2016 | Dubois | A61B 17/176 |
| 9,381,072 | B2* | 7/2016 | Furrer | A61B 17/8061 |
| 9,855,056 | B2* | 1/2018 | Furrer | A61B 17/8071 |
| 11,357,514 | B2* | 6/2022 | Furrer | A61B 17/151 |
| 12,029,458 | B2* | 7/2024 | Simpson | A61B 17/151 |
| 2016/0331427 | A1* | 11/2016 | Waizenegger | A61B 17/8071 |
| 2018/0221069 | A1* | 8/2018 | Kohler | A61B 17/8057 |
| 2022/0330992 | A1* | 10/2022 | Simpson | A61B 17/808 |
| 2023/0346500 | A1* | 11/2023 | Zille | A61B 17/80 |
| 2023/0371990 | A1* | 11/2023 | Reinauer | A61B 17/8071 |

FOREIGN PATENT DOCUMENTS

| | | |
|---|---|---|
| CN | 201894681 U | 7/2011 |
| TW | M399700 U | 3/2011 |

\* cited by examiner

*Primary Examiner* — Anu Ramana
(74) *Attorney, Agent, or Firm* — Muncy, Geissler, Olds & Lowe, P.C.

(57) ABSTRACT

A maxilla holder includes a base plate and a connecting member. One end of the connecting member is connected with the base plate which extends along a pre-designed occlusal plane while the other end of the connecting member includes at least two supporting portions. With the supporting portions abutting against the cranium, the base plate is positioned so that the maxilla is located in a pre-planned position once it is moved onto the base plate.

7 Claims, 7 Drawing Sheets

MAXILLA HOLDER AND INSTALLATION THEREOF

BACKGROUND OF INVENTION

Field of Invention

The present invention relates to a surgical aid tool, particularly to a maxilla holder.

Related Prior Art

Certain congenital and acquired factors can impact the growth of the maxilla or mandible, leading to conditions such as protrusion of the upper jaw (e.g., overbite) or protrusion of the lower jaw (e.g., underbite). These conditions can result in malocclusion, incomplete chewing of food affecting digestion, and physiological issues. Moreover, they may cause psychological concerns related to facial aesthetics and self-confidence. Corrective jaw surgery is a viable solution to address these issues by adjusting the maxilla and mandible to more suitable positions.

One step in orthognathic surgery involves cutting the maxilla from the cranium and repositioning it appropriately. The maxilla, once cut, becomes free and requires a positioning aid tool to facilitate proper placement. In conventional orthognathic surgery, the mandible 82 is often used to position the maxilla 81 (referenced in FIG. 9). Therefore, the positioning aid tool, an occlusal splint for upper and lower teeth, is designed based on computed tomography scans of the patient's head and entire oral cavity (referenced in FIG. 8). The occlusal splint 7 has lower tooth pits 71 on its bottom surface engaging with the lower teeth of the mandible and upper tooth pits 72 on its top surface located at the anticipated position for the repositioned maxilla. The upper teeth engages with the upper tooth pits 72, providing the necessary positioning (refer to FIG. 9). The method of use for the occlusal splint 7 is as follows:

First, place the occlusal splint 7 on the lower teeth of the mandible, and make sure that the lower teeth occludes with the lower teeth tooth pits 71. Then move the cut maxilla to the upper tooth pits 72 on the occlusal splint 7, and ensure that the upper teeth occludes with the tooth pits 72, when this point has been reached, it indicates that the maxilla has been moved to the intended position, as shown in FIG. 9. Then, by use wiring and fixtures to bind the upper and lower teeth together, ensuring that the maxilla 81 is securely positioned on the mandible 82.

However, the method of using the occlusal splint 7 on the mandible to determine the positioning of the cut maxilla has the following drawbacks:

1. The mandible 82, serving as the positioning base, is not fixed and can move vertically and even forward and backward due to its joint connection with the cranium 83. This lack of stability in the mandible 82 prevents precise positioning, leading to the inability to relocate the maxilla 81 to the intended position accurately.
2. The width W of the occlusal splint 7 is too wide for the small oral space, which makes the already small oral space to become even smaller, this will hinder the entire surgical procedure.
3. Since the mandible 82 is not fixed and is able to move to a limited extent, and because the width W of the occlusal splint 7 is too wide, which makes it challenging to perform the tooth binding procedure.

Furthermore, during the binding procedure, the position of the mandible 82 may move due to the binding, which will in turn alter the position of the maxilla 81, preventing it from staying in the correct location originally positioned.

SUMMARY OF THE INVENTION

To address the aforementioned issues, the present invention provides a maxilla holder that comprises of a base plate extending along a predetermined occlusal plane; a connecting member, one end of which is connected to the base plate; and at least two first supporting portions located at the end of the connecting member, used to support against the cranium.

Preferably, the connecting member includes a stem portion connected to the base plate and at least two branch portions extending in different directions from the stem portion. The two first supporting portions are formed at the end of the branch portions to support against the sides of the piriform aperture.

Furthermore, the two branch portions, apart from the ends, each has a second supporting portion to support against the sides of the anterior nasal spine.

Preferably, a depression facing the cranium is formed at the intersection of the stem portion and the at least two branch portions to accommodate the anterior nasal spine.

Preferably, the base plate forms a U-shape, with the stem portion connected at the central position of the outer edge of the base plate, and the opening angle of the two branch portions does not exceed the opening angle of the base plate.

Preferably, each first supporting portion and each second supporting portion respectively has a perforation.

Preferably, tooth pits are provided on the top surface and bottom surface of the base plate.

DETAILED DESCRIPTION OF PREFERRED EMBODIMENT

Figure 1:
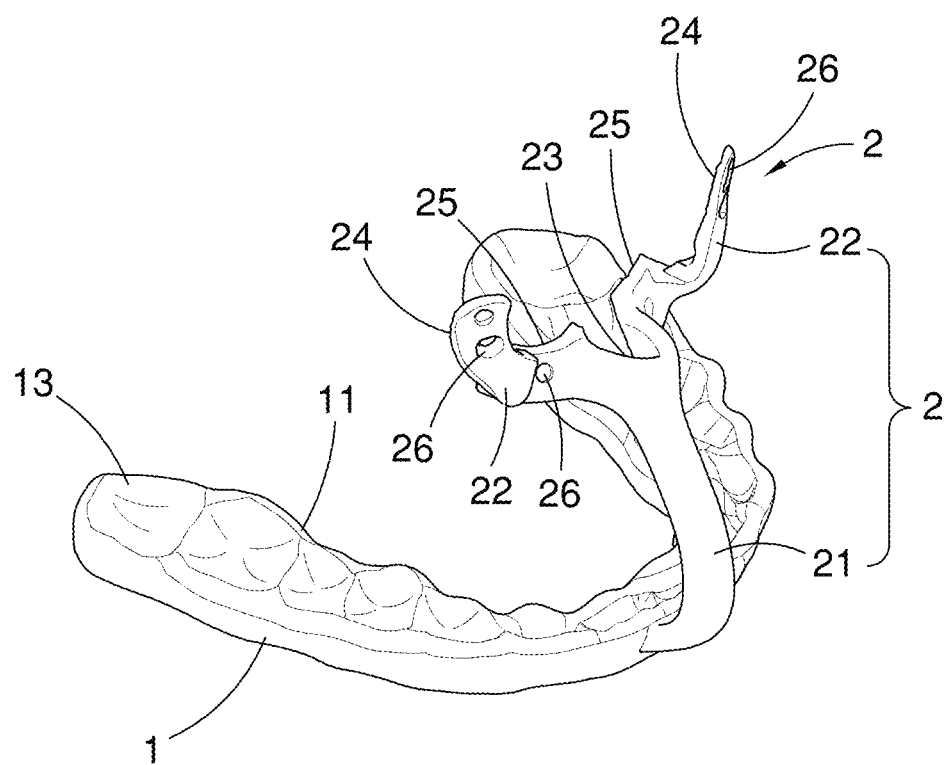
FIGS. 1 and 2 are perspective views of the present invention.
Figure 2:
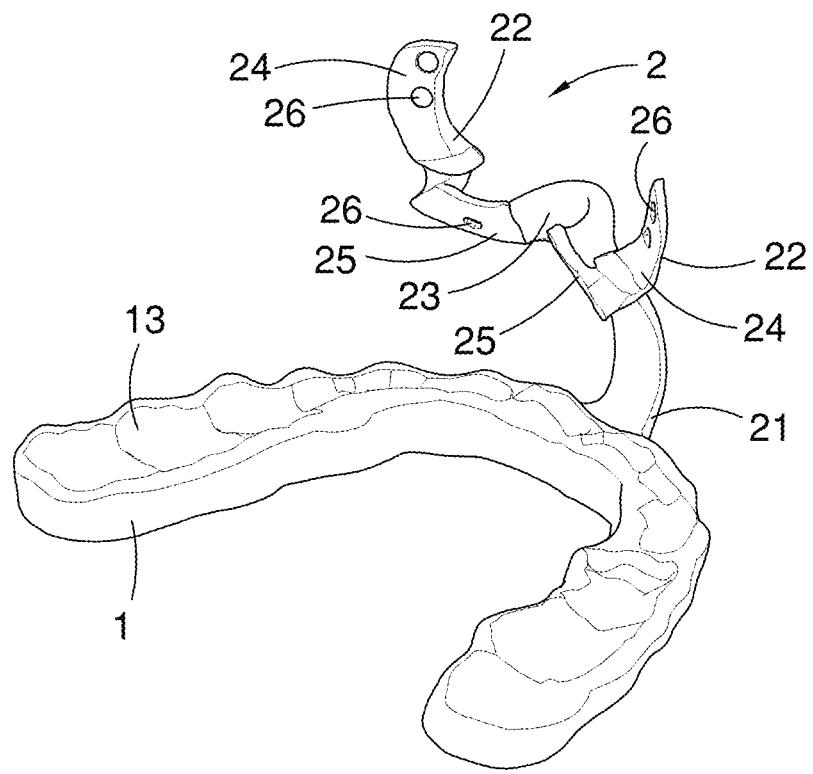
Figure 3:
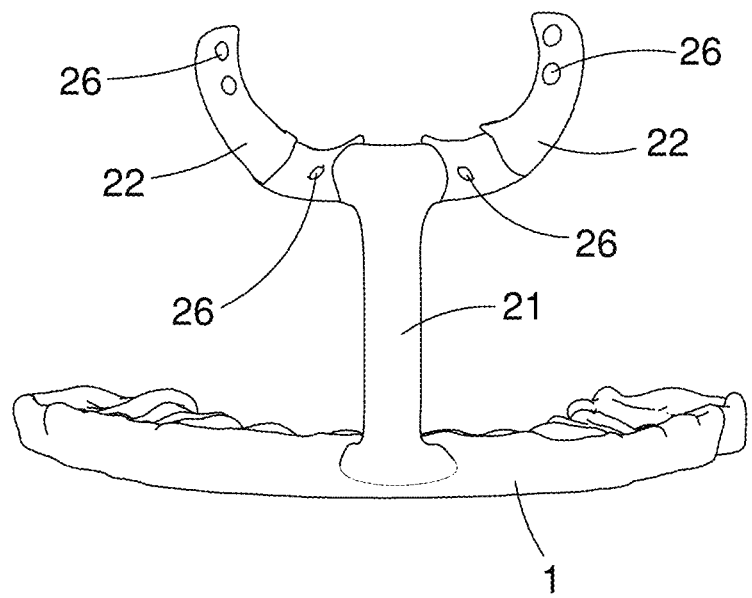
FIG. 3 is a front view of the present invention.
Figure 4:
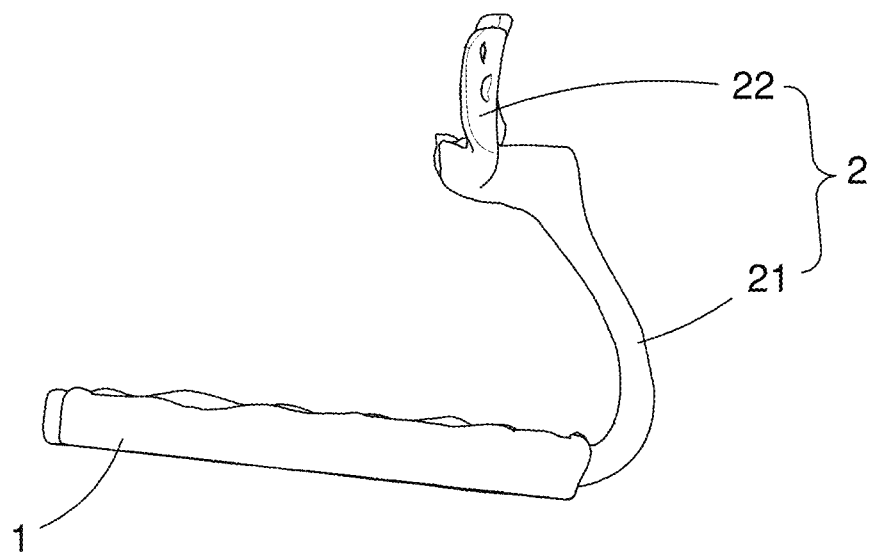
FIG. 4 is a side view of the present invention.

Refer to FIGS. 1 through 5, illustrating the maxilla holder provided by the present invention, comprising a base plate 1 and a connecting member 2. The base plate 1 forms a U-shape corresponding to the arrangement of upper and lower teeth, with a width slightly wider than the width of the teeth. The top surface 11 of the base plate 1 features tooth pits 13 complementary to the upper teeth of the maxilla, allowing the maxilla to be positioned by engaging with the upper teeth into the tooth pits 13. The connecting member 2 includes a stem portion 21 and two branch portions 22. The stem portion 21 is connected at one end to the central position of the outer edge of the base plate 1 and extends upward, while the two branch portions 22 extend in different directions from the top end of the stem portion 21. In this embodiment, the opening angle of the two branch portions 22 does not exceed that of the sides of the base plate 1.

The two branch portions 22 are connected to the stem portion 21, forming a depression 23 at the junction due to bending. The depression 23 faces the rear of the base plate 1 and creates a receiving space for the anterior nasal spine to extend into. After bending to form the depression 23, the two branch portions 22 extend upward and sequentially form a second supporting portion 25 and a first supporting portion 24 along the extension direction, wherein the first supporting portion 24 located at the end of the branch portion 22. The first supporting portion 24 is designed to abut against the sides of the piriform aperture of the cranium, with its surface shape complementary to the shape of the abutting position to ensure proper contact. The second supporting portion 25 is designed to abut against the sides of the anterior nasal spine of the maxilla, with its surface shape complementary to the shape of the abutting position to ensure proper contact.

The specific manufacturing process of the maxilla holder of the present invention begins with a computed tomography scan of the user's skull and entire mouth to construct three-dimensional models of the cranium and upper and lower jaws. Based on these models, the planned position for the detached maxilla to be repositioned is determined. This information, including the relative positions or distances between the planned positions and the cranium, is then used to locate the positions of the base plate 1, first supporting portion 24, and second supporting portion 25 of the present invention. The base plate 1 extends along the planned occlusal plane, the first supporting portion 24 abuts against both sides of the piriform aperture, and the second supporting portion 25 abuts against both sides of the anterior nasal spine. These components are then connected using the connecting member 2. Therefore, the maxilla holder of the present invention is a customized structure, and maxilla holders used by different users do not have identical shapes and sizes. However, each functional component (i.e., the base plate 1, first supporting portion 24, and second supporting portion 25) functions in the same manner to achieve the desired effect.

Figure 6:
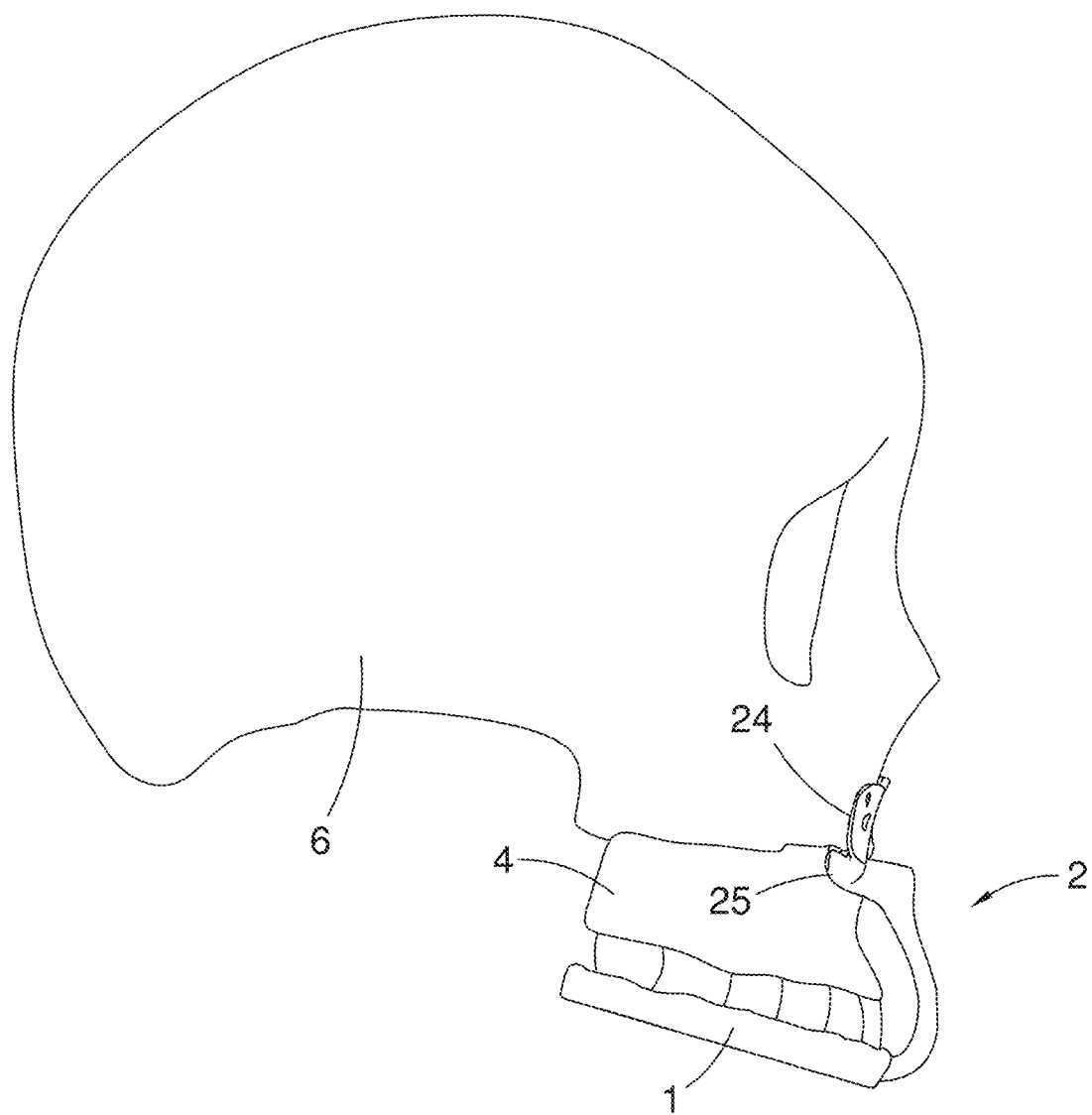
FIGS. 6 and 7 illustrate the present invention in a operational state.
Figure 7:
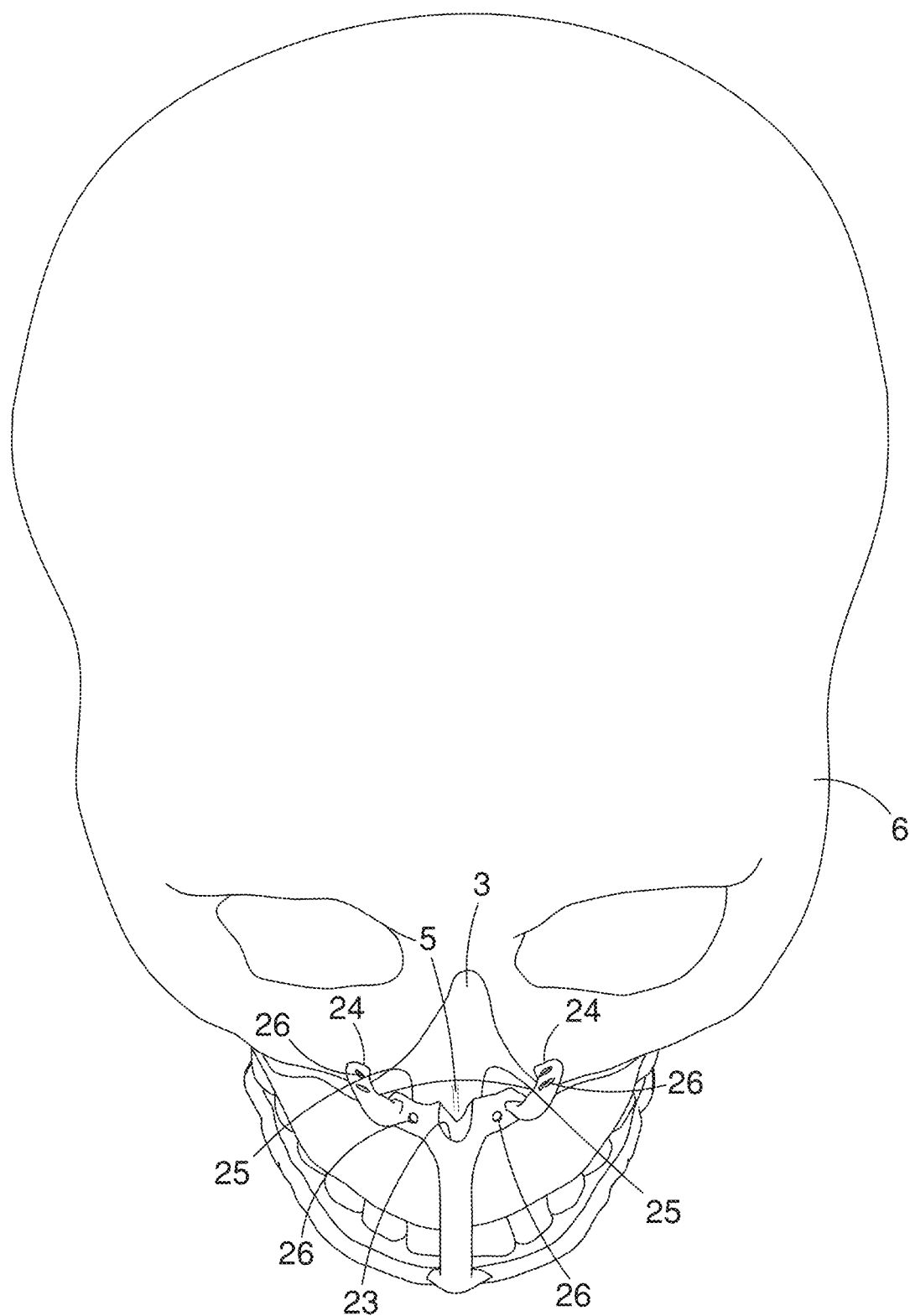
Figure 8:
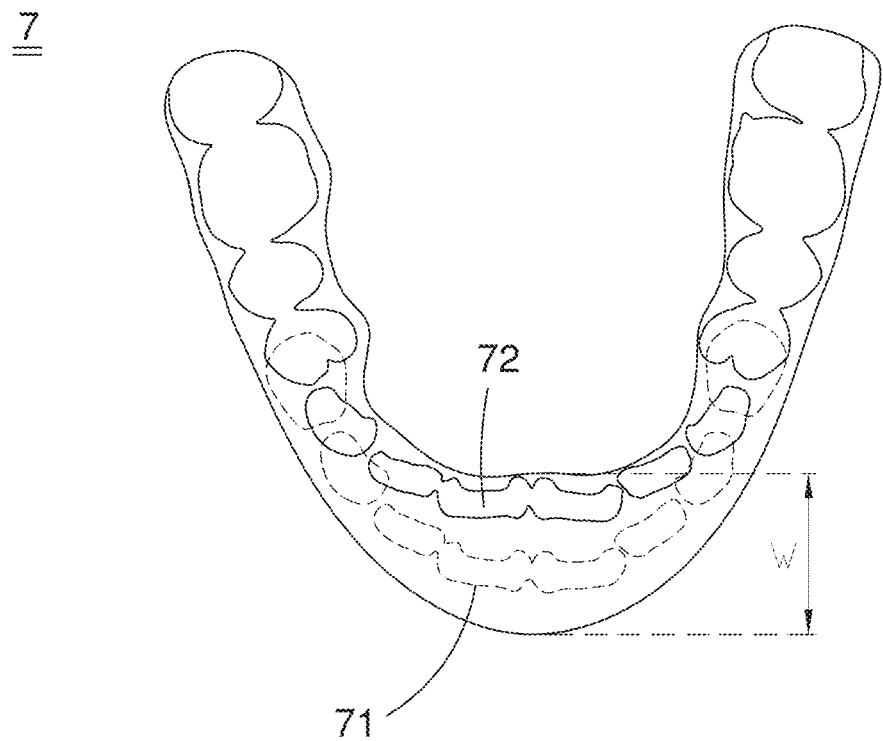
FIG. 8 is a plan view of a conventional occlusal splint.
Figure 9:
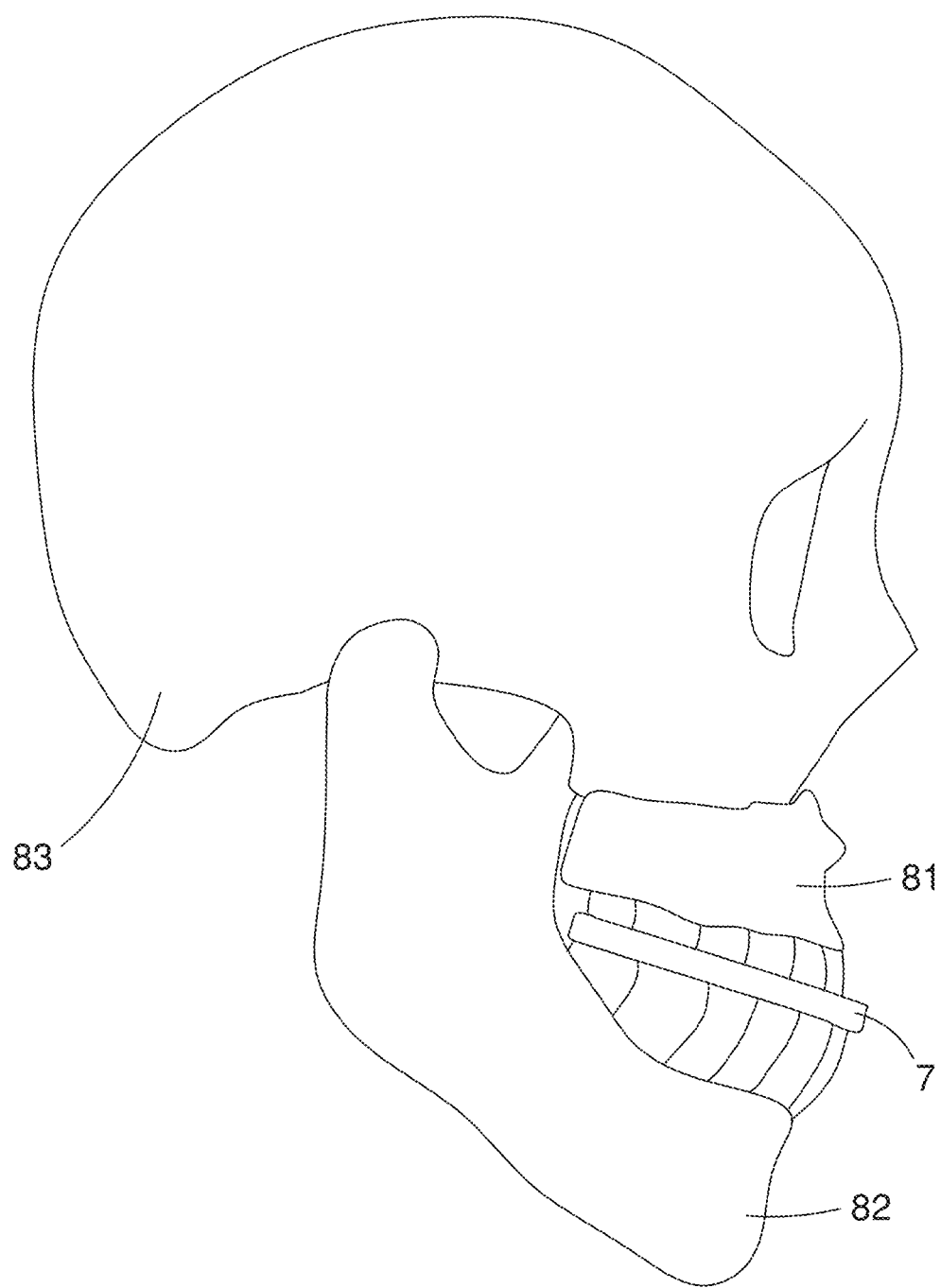
FIG. 9 illustrates a conventional occlusal splint in a operational state.

Therefore, during the actual process of positioning the maxilla, due to the fact that the locator of the present invention is designed in advance for the new position of the maxilla, once the locator is inserted into the oral cavity, as shown in FIGS. 6 and 7, simply ensuring that the two first supporting portions 24 respectively abut on both sides of the piriform aperture 3 and achieve stable abutment based on complementary shapes, the base plate 1 will automatically come to the designed position of the maxilla 4. At this point, placing the maxilla 4 onto the base plate 1 and ensuring that both sides of the anterior nasal spine 5 abut against the two second supporting portions 25, where the anterior nasal spine 5 can be accommodated within the depression 23, results in the maxilla 4 reaching the designated position. Subsequently, by engaging the upper teeth into the tooth pits 13 on the top surface 11 of the base plate 1, the maxilla 4 can be easily moved to the desired position and securely positioned.

The present invention achieves stable positioning by having the two first supporting portions 24 abut against the cranium 6. However, if there are more first supporting portions 24 abutting against the cranium 6, the precision of the positioning can be further enhanced. Accordingly, the connecting member 2 of the present invention may also include a greater number of branch portions 22 to form a greater number of first supporting portions 24.

For accurate positioning of the maxilla, the maxilla holder of the present invention may be constructed using metal materials (such as stainless steel) to increase rigidity, ensuring precise positioning without deformation during the procedure. Another advantage of using metal instruments is the ability to reduce thickness while maintaining rigidity, providing the surgeon with ample space for operation during the procedure. Alternatively, the maxilla holder of the present invention may also be made of plastic materials, although the structural thickness may be slightly larger due to rigidity requirements.

Figure 5:
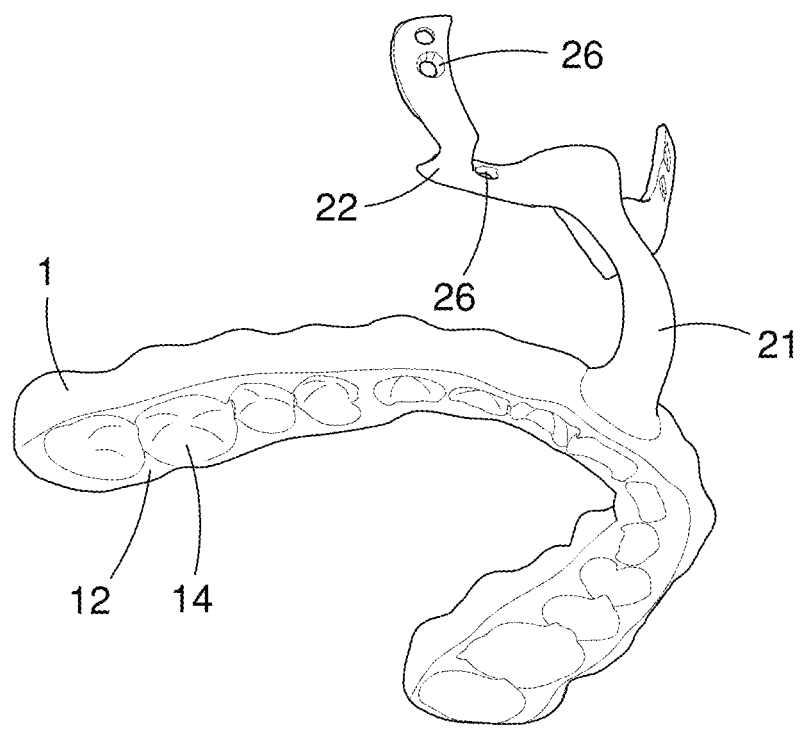
FIG. 5 is a perspective view of the present invention from another angle.

Additionally, as shown in FIG. 5, tooth pits 14 complementary to the shape of the lower teeth may also be provided on the bottom surface 12 of the base plate 1, allowing the base plate 1 to abut against the lower teeth for auxiliary positioning.

Furthermore, perforations 26 can be provided on both the two first supporting portions 24 and the two second supporting portions 25. After the first supporting portions 24 abut against the sides of the piriform aperture 3, and the second supporting portions 25 abut against the sides of the anterior nasal spine 5, bone screws can be inserted through the perforations 26 and into the cranium 6 and maxilla 4. This secures the positioning device of the present invention to the cranium 6 and maxilla 4, thereby strengthening the positioning foundation of the present invention.

In view of the above, the distinguishing feature of the present invention lies in utilizing the fixed cranium 6 as the positioning foundation. When the first supporting portions 24 are abutted against and secured to the cranium 6, they effectively serve as an extension of the cranium 6, allowing the maxilla 4 to be precisely positioned by easily placing it on the base plate 1. This is different from previous techniques that used the movable mandible as the positioning foundation for positioning the maxilla, resulting in more precise positioning.

According to the aforementioned description of the maxilla holder of the present invention, the installation process of the maxilla holder includes the following: Place the two first supporting portions 24 against the two sides of the patient's piriform aperture 3 on the cranium 6. Then insert at least two screws through the perforations 26 of the two first supporting portions 24 and screw them into the cranium 6, so that the two first supporting portions 24 are respectively pressed against and secured on either side of the piriform aperture 3. At this point, the base plate 1 will be positioned within the patient's oral cavity and in the desired correct position. This position, and the relative positions of the base plate 1 and the two first supporting portions 24 are designed based on the results of a computed tomography (CT) scan prior to the making of the maxilla holder. Next, place the cut maxilla 4 onto the base plate 1, as shown in FIG. 6. At this point, the maxilla 4 is positioned in the correct location. Preferably, two screws can also be inserted through the perforations 26 of the two second supporting portions 25 and screwed into the maxilla 4, so that the maxilla 4 is pressed against and fixed to the two second supporting portions 25.

Since the maxilla holder is fixed to the cranium 6 by the two first supporting portions 24 and will not move further, and because the width of the base plate 1 is smaller (as its bottom surface 12 can optionally omit the tooth pits 14), the issues previously arising from using the mandible to position the maxilla can be resolved.

What is claimed is:
1. A maxilla holder comprising:
   a base plate, having a top surface, a bottom surface and a plurality of tooth pits formed on the top surface, wherein the tooth pits are capable to receive capable of receiving teeth situated on a maxilla respectively;

a stem portion, having a first end and a second end, the first end connected to the base plate;

two branch portions, extending in different directions from the second end of the stem portion respectively; and two first supporting portions, each first supporting portion connected to a respective branch portion wherein the two first supporting portions are configured to abut against two sides of a piriform aperture of a cranium respectively.

2. The maxilla holder as recited in claim 1, further including two second supporting portions connected to the two branch portions respectively, wherein each second supporting portion is positioned between the second end of the stem portion and each first supporting portion, and wherein the two second supporting portions are capable to abut against two sides of an anterior nasal spine of the cranium respectively.

3. The maxilla holder as recited in claim 2, wherein each of the second supporting portions has a perforation.

4. The maxilla holder as recited in claim 2, wherein the second end of the stem portion has a depression facing the cranium, the depression being capable to accommodate the anterior nasal spine.

5. The maxilla holder as recited in claim 1, wherein the base plate is U-shaped, and has a front surface and a back surface, wherein the first end of the stem portion is connected at a central position on the front surface of the base plate.

6. The maxilla holder as recited in claim 1, wherein each of the first supporting portions has a perforation.

7. The maxilla holder as recited in claim 1, wherein the base plate has a plurality of tooth pits formed on the bottom surface, wherein the tooth pits on the bottom surface are capable to receive lower teeth situated on a mandible respectively.

* * * * *